United States Patent [19]

Ehlers

[11] Patent Number: 4,971,033
[45] Date of Patent: Nov. 20, 1990

[54] FLEXISCOPE TUBE STIFFENER

[76] Inventor: Robert L. Ehlers, 414 Rehnberg Pl., W. St. Paul, Minn. 55118

[21] Appl. No.: 506,294

[22] Filed: Apr. 9, 1990

[51] Int. Cl.⁵ .............................................. A61B 1/00
[52] U.S. Cl. .......................................................... 128/4
[58] Field of Search ........................................ 128/4, 6

[56] References Cited

U.S. PATENT DOCUMENTS

| | | | |
|---|---|---|---|
| 4,464,175 | 8/1984 | Altman et al. | 128/4 X |
| 4,598,698 | 7/1986 | Siegmund | 128/4 |
| 4,737,142 | 4/1988 | Heckele | 128/6 X |
| 4,784,133 | 11/1988 | Macklin | 128/6 X |
| 4,800,870 | 1/1989 | Reid, Jr. | 128/6 |
| 4,815,450 | 3/1989 | Patel | 128/6 |
| 4,928,669 | 6/1989 | Sullivan | 128/4 |

Primary Examiner—William H. Grieb
Attorney, Agent, or Firm—Merchant, Gould, Smith, Edell, Welter & Schmidt

[57] ABSTRACT

A flexiscope is disclosed including a working channel, said channel serving to straighten e.g. controlling the rigidity of the flexiscope by applying fluid or pneumatic pressure to said channel.

10 Claims, 5 Drawing Sheets

FLEXISCOPE TUBE STIFFENER

FIELD OF THE INVENTION

The present invention relates to medical devices and more particularly to flexiscopes or colon scopes.

BACKGROUND

Flexiscopes are well known in the medical art. A flexiscope is a device used to examine a patient experiencing problems in the colon and lower reaches of the digestive tract. A flexiscope generally includes a flexible tube and a control housing. The flexible tube has a plurality of optical fibers to transmit light to the remote end of the flexiscope. Other fibers are used to return reflected light from the remote end to the control housing e.g. the viewing end of the flexiscope.

Over the years, various problems have been recognized with the construction and operation of the flexiscope and many improvements have been developed.

One problem in particular persists and is inherent in the existing structure of the flexiscope. In particular, the elongated portion of the flexiscope is quite flexible. This is necessary in order to follow the contours of the colon. The colon follows a tortious path, after doubling back on itself in sharp S-shaped curves. In order for it to be sufficiently flexible to follow the tortious path through the colon, the flexiscope inserted in the colon wall may loop and/or double back on itself, sometimes kinking. In some instances the looping and doubling back consumes the entire length of the scope within a relatively short path in the colon. In some patients the colon is extraordinarily long and has extra loops, especially at the lower end, and the flexiscope tube tends to loop or kink in such a colon to an even greater extent.

The present invention overcomes such problems by controlling rigidity, the direction and positioning of the flexiscope to gain full usage of the length of the flexible tube so that the viewing end may reach further into the colon.

Summary of the Proposed Invention

The existing invention provides a medical device e.g. a flexiscope including a control portion and an elongated flexible tube carrying a plurality of fiber optics that permits observation of the interior of the colon. The device may include a plurality of fibers for transporting light along the tube to the site being observed deep within the colon. Other fiberoptics are used to return the reflected light (e.g. view of the site) to a lens. A further feature of the flexiscope is a larger channel entending length of the tube through which various instruments may be threaded to perform biopsies, sever palops etc.

The existing device may be similar in structure to the Pentax Flexible Fiberoptic Sigmoidoscope Model 35 or other such devices made by Olympus with certain modifications or improvements. Such devices have been used in the past for observation within the colon.

The proposed invention modifies and improves such previously existing scopes to permit control of the rigidity, direction and orientation of the remote end of the elongated tube within the colon. The present device includes a wire controlled cannula (similar to a bicycle brake cable) attached to the base of rubberized or pliable plastic plug and a control wire running its length attached to a solid cone structure within the plug. Retracting the cone by pulling the wire causes the plug to expand to provide a seal at the selected site within the working channel of the flexible tube having a pneumatic or hydraulic zone which when pressurized straightens the tube.

In the Drawings

Detailed Description

Figure 1:
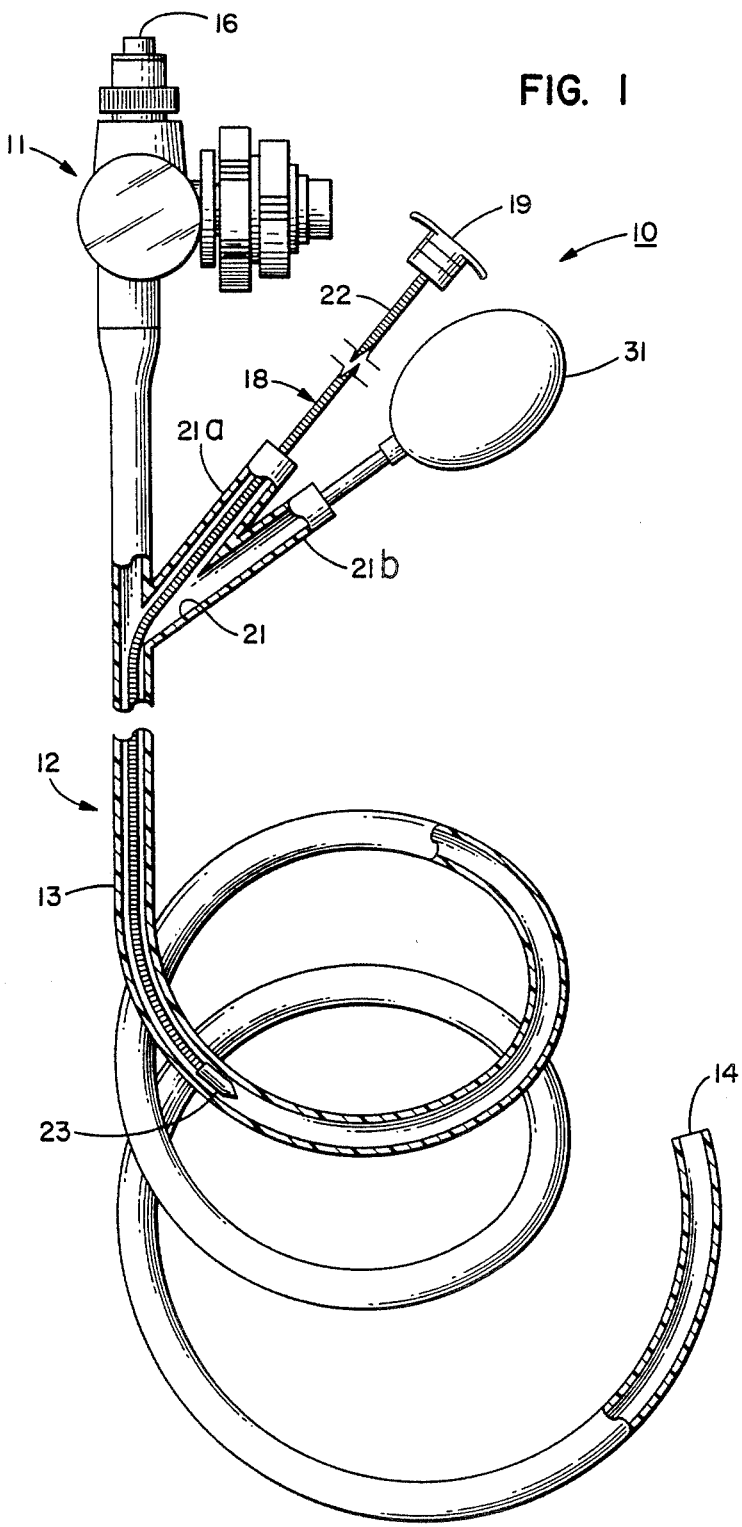
FIG. 1 illustrates a flexiscope disposed in a first position within a colon with a plurality of loops or overlapping portions of the elongated tube.

The flexiscope 10 (FIGS. 1—3) includes a control and observation housing 11 and an elongated tube 12. The tube 12 has a flexible or bendable portion 13 intermediate the forward end 14 and the housing 11. The tube 12 has an image transmitting optical system 15 commencing at the end portion 14 and terminating at the eye piece 16 of the control housing 11. In order to illuminate the object, the optical system 15 may include a plurality of light conducting fibers 15a which are adjacent to a plurality of optical fibers 15b that return an image to the lens 16.

Figure 2:
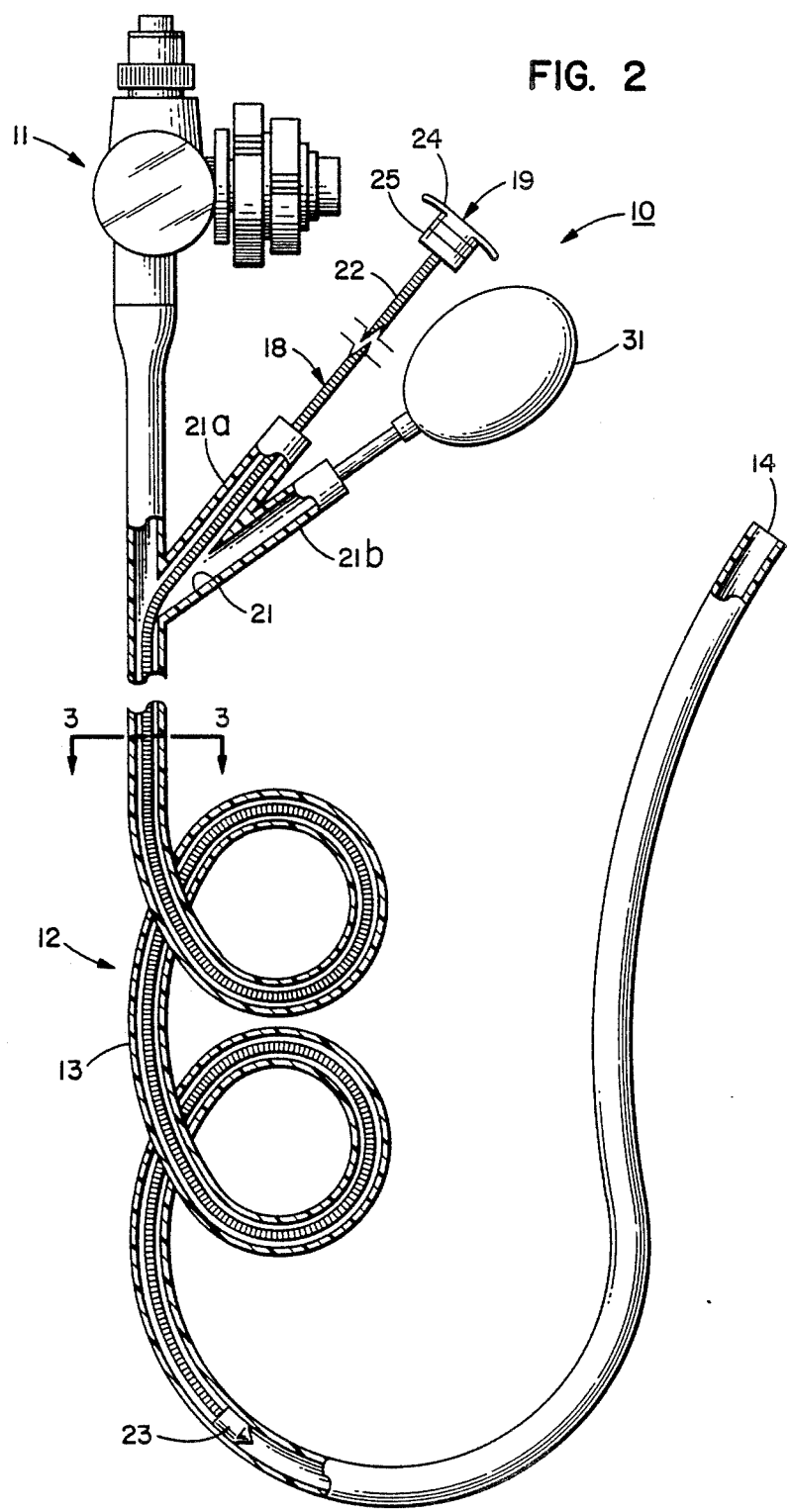
FIG. 2 is a cross-sectional view of the device of FIG. 1 in another position of operation in which the loops have been straightened.
Figure 3:
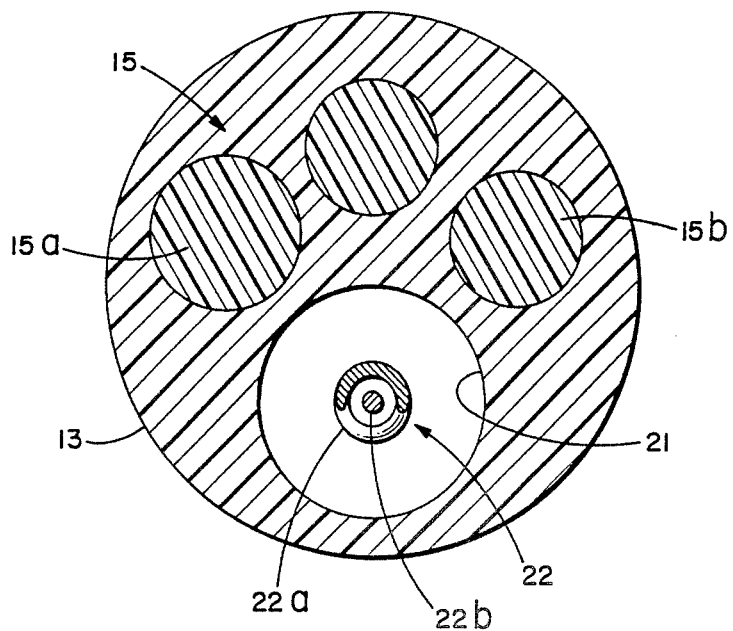
FIG. 3 is a cross-sectional view taken along the line 3—3 of FIG. 2.

The tube 12 includes a working channel 21 (FIG. 3) which normally serves as a biopsy channel but in the present invention serves a special function. The rigidity of the flexible portion 13 (FIG. 1) may be controlled through use of the working channel 21 as hereinafter described. The working channel 21 has a pair of ports or entrances 21a and 21b near the control housing 11 (FIG. 2). The working channel 21 may extend substantially the complete length of the elongated tube 12. The present invention has a cannula section 18 including a control portion 19, a sheathed wire 22 and a plug 23. The plug 23 is secured at the forward end of the wire 22. The sheathed wire 22 may be a coaxial structure including a wrapping 22a and a wire 22b. The wrapping 22a serves as a noncompressable tube within which the wire 22b may be moved.

Figure 8:
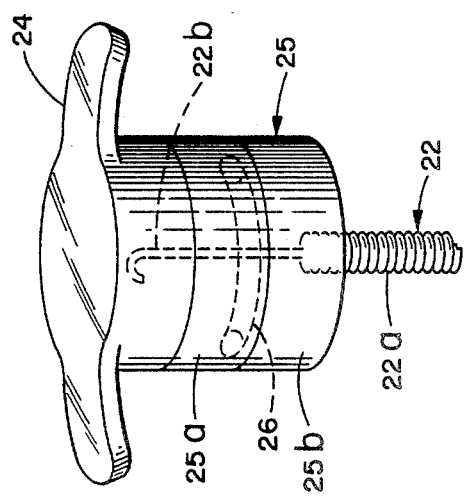
FIGS. 7 and 8 illustrate the control portion of the pneumatic or hydraulic section.
Figure 7:
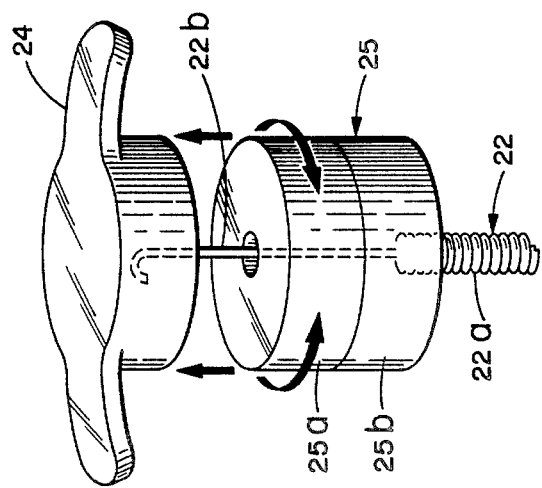

The control portion 19 (FIGS. 1, 7 and 8) may have a handle 24 and a cap 25. The handle 24 is secured to the end of the wire 22b. The cap 25 has two portions 25a and 25b. The wrapping 22a is secured to portion 25b of cap 25. The wire 22b extends through cap portions 25a and 25b. A seal 26 is provided in cap 25 between cap portions 25a and 25b.

The seal 26 is of a conventional type which may be tightened about the wire 22b by twisting cap portion 25a with respect to cap portion 25b. The wire 22b extends through the seal 26 in cap 25 thereby making the tube working channel 21 fluid or pneumatic tight and securing the wire with respect to wrapping 22a when in operation.

The plug 23 is of an appropriate dimension which when compressed or squared, will snugly engage the walls of the tube 21 to provide a substantially liquid or pneumatic tight engagement. The plug may be of a flexible polymeric material. The plug 23 desirably is of a construction that permits expansion of the plug diameter such as by retraction of the wire with respect to the cannula sheath. In other words, the wire moves the cone 23a (or forward caps) rearwardly while the cannula attached to the rear portion 23c prevents the plug 23 from moving thereby shortening and expanding the diameter of the plug 23. The expanded plug 23 provides a fluid or pneumatic tight blockage in the working channel 21.

The device 10 includes a fluid or pneumatic pump, for example, in the form of a compressible ball 31 which communicates with the tube 21 through port 21b so as to provide fluid or pneumatic pressure upon demand. For example, the ball 31 may contain air or a liquid such as water. When the ball 31 is compressed, the fluid or gas moves into the tube 21 creating pressure within the tube 21. The pressure in turn causes the tube to straighten (or erect) (FIG. 2), thus facilitating the advancement of the forward end or tip 14 of the tube 12 further into the colon. Once the loops have partially or completely been removed thereby further extending the tube 12, the fluid may be bled off thereby making the tube 12 once again flexible.

Operation of the Invention

While the operation of the invention is apparent from the afore-description, it will be further described to assure a more complete understanding of the invention.

After advancing the control wire 22 and plug 23 to the desired position and firmly positioning the plug 23 by expanding the plug walls against those of the working channel 21, the operator injects fluid or air (gas) under controlled pressure to stiffen the flexiscope tube 12, or a segment thereof to prevent, eliminate or shorten loops and kinks in the tube 12 to facilitate the advancement of the tube 12 along the colon of the patient.

By injecting and retaining liquid or air (gas) under controlled pressure in the working channel the tube will gently stiffen and tend to straighten itself, similar to a garden hose which, without water pressure, tends to loop and kink, but which, under pressure, expands, becomes rigid and less prone to kinking.

Figure 4:
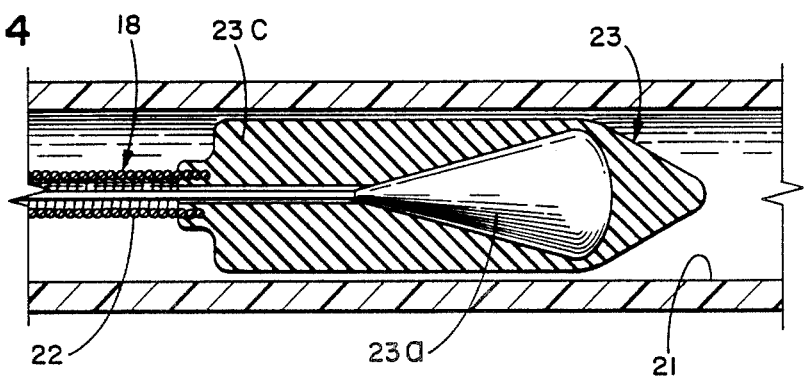
FIGS. 4 through 6 are views showing the plug in various positions of operation.
Figure 5:
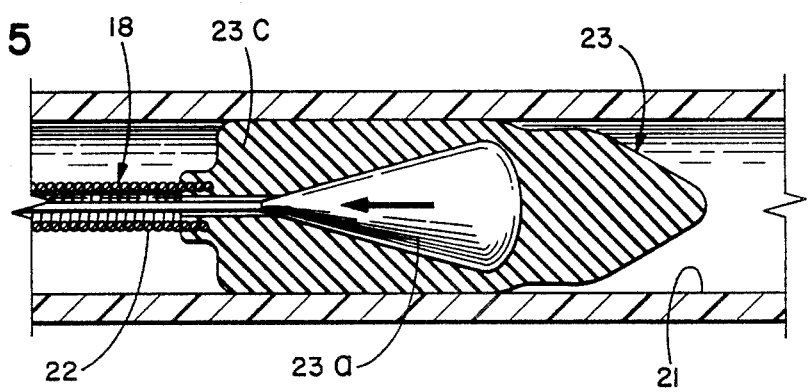
Figure 6:
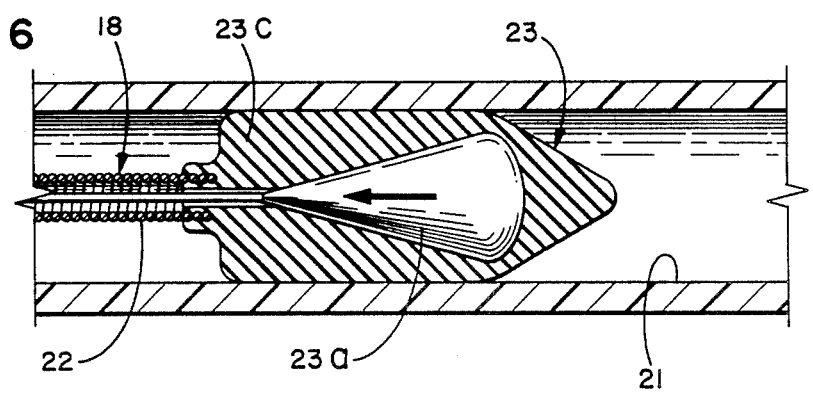

The plug 23 sheathed by rubber, neoprene or other pliable material is attached at the base to a wire-wrapped cover cannula 18 and contains within it a moveable cone 23a or is capped with a smaller diameter plate attached by a sheathed wire to a control at the base of the instrument. Retraction of the interior wire by the operator, causes the circumference of the plug to expand against the wall of the working channel 21 sealing it. (FIG. 4).

The operator then injects fluid or air (gas) into the working channel under pressure controlled by the operator (with appropriate control limits to prevent excess pressure and scope rigidity) (FIG. 2). As hydro or pneumatic pressure builds, the flexiscope tube, or part thereof between the base and the expanded plug, in place in the colon, will become more rigid and, with the outer end fixed and under operator control, will allow the operator to ease the end of the tube further along the colon.

When the pressurized scope tube has corrected itself by shortening the loop(s) in the lower end of the colon, flexibility can be restored by bleeding off some or all of the pressure and the scope may be advanced normally. When the viewing end of the flexiscope 14 is in position and the operator desires to do other work, the pressure can be bled off from the working channel by extending the control wire which releases the plug and the cannula can be withdrawn together with the plug. The flexiscope is then used in its normal fashion.

The plug could be, but is not expected to be, used in the last two to three inches of the scope since the operator will wish to retain the flexibility and control of the tip during the advancement of the instrument. Also extra rigidity in the tip may pose a danger of perforating the colon wall. The rigidity of the flexiscope is normally expected to be enhanced only temporarily after the scope has been inserted past the loop(s) in order to worm (telescope) the colon wall over the tube reducing the loop(s) and extending the useful length of the scope, but it may be found useful in the initial entry of a colon loop by providing extra temporary rigidity not normally present in the flexiscope in order to better traverse curves and loops of the colon.

While certain preferred embodiments of the present invention are disclosed, it is to be recognized that various modifications may be made without departing from the broader scope of the present invention.

What is claimed is:

1. In a flexiscope comprising a control housing and an elongated flexible tubing, said control housing including a light source and a lens, said elongated tubing including a plurality of optical fibers extending from said control housing through the length of said elongated tubing for transmitting light to an observation site and for returning the reflected light to said lens, said elongated tubing further including a working channel, said working channel extending from adjacent said control housing to the remote end of said elongated tubing, the improvement comprising a plug slidably received within said working channel, means for controlling the location of said plug in said working channel, and means for fluid pressurizing said working channel thereby controlling the rigidity of the pressurized portion of said working channel.

2. The device of claim 1 wherein said plug includes means for expanding the diameter of said plug to provide sealing engagement between said plug and the walls of said working channel.

3. The device of claim 1 wherein said plug includes means for compressing the length of said plug thereby expanding the diameter of said plug to provide sealing engagement between said plug and said fluid channel.

4. The device of claim 1 wherein said fluid tube includes a coiled wire cannula for controlling the location of said plug along said channel.

5. The device of claim 4 wherein said cannula and plug includes means for expanding the diameter of said plug.

6. The device of claim 1 wherein said fluid channel includes a fluid charging bulb or foot pump, communicating with said working channel.

7. In a flexiscope comprising a control housing and an elongated flexible tubing, said control housing including a light source and a lens, said elongated tubing including a plurality of optical fibers extending from said control housing through the length of said elongated tubing for transmitting light to an observation site and for returning the reflected light to said lens, said elongated tubing further including a working channel, said working channel extending from adjacent said control housing to the remote end of said elongated tubing, the improvement comprising a plug slidably received within said working channel, said plug including means for expanding the diameter of said plug to provide sealing engagement between said plug and said working channel, means for controlling the location of said plug in said fluid channel, and means for fluid pressurizing said fluid channel for controlling the rigidity of the pressurized portion of said working channel.

8. The device of claim 7 wherein said plug includes means for compressing said plug thereby expanding the diameter of said plug to provide a sealing engagement between said plug and said working channel.

9. The device of claim 8 wherein said cannula includes a wire to be retracted to compress the diameter of the plug against the walls of the working channel.

10. The device of claim 9 wherein said working channel includes a fluid or gas charging bulb or foot pump communicating with said working channel.

* * * * *

UNITED STATES PATENT AND TRADEMARK OFFICE
CERTIFICATE OF CORRECTION

PATENT NO. : 4,971,033

DATED : November 20, 1990

INVENTOR(S) : Robert L. Ehlers

It is certified that error appears in the above-identified patent and that said Letters Patent is hereby corrected as shown below:

Column 2, line 22, "thc" should read --the--.

Column 1, line 23, "clongated" should read --elongated--.

Column 1, line 52, "entending" should read --extending--.

Signed and Sealed this

Eighth Day of September, 1992

Attest:

DOUGLAS B. COMER

Attesting Officer      Acting Commissioner of Patents and Trademarks